US006107343A

United States Patent [19]

Sallmann et al.

[11] Patent Number: 6,107,343

[45] Date of Patent: Aug. 22, 2000

[54] OPHTHALMIC AND AURAL COMPOSITIONS CONTAINING DICLOFENAC POTASSIUM

[75] Inventors: Alfred Sallmann, Bottmingen; György Lajos Kis, Triboltingen, both of Switzerland; Wolfgang Blum, Weil am Rhein, Germany; Alica Huxley, Binningen, Switzerland

[73] Assignee: Novartis AG, Basel, Switzerland

[21] Appl. No.: 09/223,198

[22] Filed: Dec. 30, 1998

Related U.S. Application Data

[62] Division of application No. 08/809,434, Aug. 27, 1997, Pat. No. 5,891,913, which is a continuation of application No. PCT/EP95/03844, Sep. 28, 1995.

[30] Foreign Application Priority Data

| | | | |
|---|---|---|---|
| Oct. 10, 1994 | [EP] | European Pat. Off. | 94810589 |
| Sep. 18, 1995 | [EP] | European Pat. Off. | 95810574 |

[51] Int. Cl.$^{7}$ .................................................. A61K 31/195

[52] U.S. Cl. .......................... 514/567; 514/912; 514/913

[58] Field of Search .................................... 514/567, 912, 514/913

[56] References Cited

U.S. PATENT DOCUMENTS 4,960,799 10/1990 Nagy ....................................... 514/567

FOREIGN PATENT DOCUMENTS

0306984A1 9/1988 European Pat. Off. .
0390071A1 3/1990 European Pat. Off. .
592348 10/1993 European Pat. Off. .
2192539 6/1986 United Kingdom .

OTHER PUBLICATIONS

Diclofenac–K (50 and 100)mg and placebo in the Acute Treatment of Migraine, C. Dahlof, et al., Cephalalgia 13, pp. 117–123, 1993.

Amoxicillin Comparative Double–Blind Study in Ent Infections Clinical Evaluation of Diclofenac Potassium vs. Placebo, Hospital Infantil Mexico, pp. 50–56,1988. (English abstract).

The Treatment of Upper Respiratory Trace and Ear Inflammatory Non–Infectious Conditions with NSAID A Comparative Rndomized Trial with Nimesulide and Potassium Diclofenac, Oliveira, D.D., pp. 87–91, 1991. (English abstract).

*Primary Examiner*—Zohreh Fay
*Attorney, Agent, or Firm*—R. Scott Meece; Robert J. Gorman, Jr.

[57] ABSTRACT

The present invention describes an ophthalmic composition comprising diclofenac potassium, the use of said composition as a medicament for treating inflammatory conditions of the eye, for treating glaucoma or for treating ear inflammatory and/or painful conditions (otitis); as well as the use of diclofenac potassium in the preparation of a pharmaceutical composition for treating any inflammatory condition of the eye, for treating glaucoma or for treating ear inflammatory and/or painful conditions (otitis).

7 Claims, No Drawings

OPHTHALMIC AND AURAL COMPOSITIONS CONTAINING DICLOFENAC POTASSIUM

This is a divisional of application Ser. No. 08/809,434, filed Aug. 27, 1997, now U.S. Pat. No. 5,891,913 which is a continuation of PCT/EP95/03844, filed Sep. 28, 1995.

The present invention describes an ophthalmic composition comprising diclofenac potassium, the use of said composition as a medicament for treating inflammatory conditions of the eye, for treating glaucoma or for treating ear inflammatory and/or painful conditions (otitis); as well as the use of diclofenac potassium in the preparation of a pharmaceutical composition for treating any inflammatory condition of the eye, for treating glaucoma or for treating ear inflammatory and/or painful conditions (otitis).

Hitherto, predominantly corticosteroids have been used for the treatment of relatively severe acute or chronically recurrent inflammatory symptoms in the eye. The immunosuppressant action of these substances, however, conceals the risk of a deterioration in the clinical picture as a result of a bacterial or viral infection. Therefore, considerable efforts are still made, to develop potent non-steroidal anti-inflammatory agents and to introduce them into ophthalmological therapy.

EP 242 328 describes for example a medicament for the treatment of inflammations of the eye, which medicament comprises sodium 2-[(2,6-dichlorophenyl)amino]-phenyl acetate, known as diclofenac sodium.

Diclofenac-potassium, is chemically described as potassium 2-[(2,6-dichlorophenyl)amino]-phenyl acetate. It is known as a non-steroidal anti-inflammatory drug (NSAID). A Norwegian publication, Cephalalgia 13, 117–123(1993), describes for example the use of diclofenac potassium in the acute treatment of migraine.

A stabilized aqueous solution of pharmaceutically acceptable salts of 2-[(2,6-dichlorophenyl)amino]-phenyl acetic acid for ophthalmic use is disclosed in U.S. Pat. No. 4,960,799. Diclofenac potassium is not specifically disclosed in said application. Accordingly, all claims and working examples of said application disclose either diclofenac sodium or its free acid as a pharmaceutically active ingredient. Hence, said application is clearly directed towards the provision of a stable aqueous solution of a pharmaceutically acceptable salt of 2-[(2,6-dichlorophenyl)amino]-phenyl acetic acid containing an effective amount of a pharmaceutically acceptable salt of ethylenediamine tetraacetic acid.

Surprisingly it was found, that the potassium salt of 2-[(2,6-dichlorophenyl)amino]-phenyl acetic acid, diclofenac potassium, is especially suitable to treat inflammatory ocular processes in general. It has been demonstrated that for example the ocular penetration of diclofenac potassium is much superior in comparison to the corresponding diclofenac sodium. In addition to said advantage, pharmacological studies show a much better topical tolerance, e.g. ocular tolerance, and efficacy of diclofenac potassium in comparison to diclofenac sodium and also a surprisingly short onset of action as well a long lasting duration of action e.g. in the eye.

Therefore the present invention relates to an ophthalmic composition for treating inflammatory ocular conditions, for treating glaucoma or for treating ear inflammatory and/or painful conditions (otitis), which composition comprises a therapeutically effective amount of diclofenac potassium and a carrier.

The present invention relates also to an ophthalmic composition for treating inflammatory conditions of the eye, which composition comprises a therapeutically effective amount of diclofenac potassium and a carrier.

The present invention relates also to an ophthalmic composition, which comprises a therapeutically effective amount of diclofenac potassium, a carrier and a stabilizer.

The present invention relates also to an ophthalmic composition, which comprises a therapeutically effective amount of diclofenac potassium, a carrier and a solubilizer.

The present invention relates also to an ophthalmic composition, which comprises a therapeutically effective amount of diclofenac potassium, a carrier, a stabilizer and a solubilizer.

The present invention relates also to an ophthalmic composition, which comprises a therapeutically effective amount of diclofenac potassium, a carrier, a solubilizer, a stabilizer and a complexing agent.

The present invention relates also to an ophthalmic composition, which comprises a therapeutically effective amount of diclofenac potassium, a carrier, a solubilizer, a stabilizer, a complexing agent and a tonicity enhancing agent.

The present invention relates also to an ophthalmic composition, which comprises a therapeutically effective amount of diclofenac potassium, a carrier, a solubilizer, a stabilizer, a complexing agent, a tonicity enhancing agent and a buffer.

The present invention relates also to an ophthalmic composition, which comprises a therapeutically effective amount of diclofenac potassium, a carrier, a solubilizer, a stabilizer, a complexing agent, a tonicity enhancing agent, a buffer and a preservative.

The present invention relates also to an ophthalmic composition, which comprises a therapeutically effective amount of diclofenac potassium and a carrier, and is further comprising one or more of the excipients selected from the group consisting of buffers, complexing agents, tonicity enhancing agents, preservatives and fillers.

The present invention relates also to an ophthalmic composition, which comprises a therapeutically effective amount of diclofenac potassium, a carrier and a stabilizer, and is further comprising one or more of the excipients selected from the group consisting of buffers, complexing agents, tonicity enhancing agents, preservatives and fillers.

The present invention relates also to an ophthalmic composition, which comprises a therapeutically effective amount of diclofenac potassium, a carrier and a solubilizer, and is further comprising one or more of the excipients selected from the group consisting of buffers, complexing agents, tonicity enhancing agents, preservatives and fillers.

The present invention relates also to an ophthalmic composition, which comprises a therapeutically effective amount of diclofenac potassium, a carrier, a solubilizer and a stabilizer, and is further comprising one or more of the excipients selected from the group consisting of buffers, complexing agents, tonicity enhancing agents, preservatives and fillers.

Another aspect of the present invention is the use of diclofenac potassium and a carrier in the preparation of a pharmaceutical composition for treating inflammatory ocular conditions, for treating glaucoma or for treating ear inflammatory and/or painful conditions (otitis).

The present invention relates also to the use of diclofenac potassium and a carrier in the preparation of a pharmaceutical composition for treating inflammatory ocular processes.

The present invention relates also to the use of diclofenac potassium, a carrier and a stabilizer in the preparation of a pharmaceutical composition for treating inflammatory ocular conditions, for treating glaucoma or for treating ear inflammatory and/or painful conditions (otitis).

The present invention relates also to the use of diclofenac potassium, a carrier, a stabilizer and a solubilizer in the preparation of a pharmaceutical composition for treating inflammatory ocular conditions, for treating glaucoma or for treating ear inflammatory and/or painful conditions (otitis).

Still another aspect of the present invention is a method of treating inflammatory ocular conditions, which method comprises administering topically to the eye of a patient requiring such treatment a therapeutically effective amount of an ophthalmic composition comprising diclofenac potassium and a carrier.

The present invention relates also to a method of treating inflammatory ocular conditions, which method comprises administering topically to the eye of a patient requiring such treatment a therapeutically effective amount of an ophthalmic composition comprising diclofenac potassium, a carrier and a stabilizer.

The present invention relates also to a method of treating inflammatory ocular conditions, which method comprises administering topically to the eye of a patient requiring such treatment a therapeutically effective amount of an ophthalmic composition comprising diclofenac potassium, a carrier, a stabilizer and a solubilizer.

In the present invention, treating inflammatory ocular conditions means, treating all ophthalmological diseases involving inflammatory processes, whatever the causes are. Examples for such causes are e.g. allergic or non-allergic inflammation, immune and non-immune processes, acute or chronic disease. Examples for such treatments of ocular inflammations are the inhibition of miosis during ocular surgery, prevention or treatment of ocular pain during these processes or consequent upon surgery, inhibition of photophobia, treatment of uveitis or ocular inflammation of any cause and the like. Post operative inflammations are for example, of the type associated with cataract removal or photo-refractive surgery or incisional refractive surgery, trabeculectomy and combined procedures thereof, painful eye-conditions (including photophobia and post-operative pain), pain associated with trauma or foreign bodies, prevention and treatment of macular edema (idiopathic or associated with surgical interventions or diabetes) and inhibition of miosis.

According to the present invention an ophthalmic composition may also be used for treating glaucoma in connection with non-inflammatory induced elevated intraocular pressure associated with administered or endogenous glucocorticoids.

According to the present invention an ophthalmic composition may also be used for treating ear inflammatory and/or painful conditions (otitis).

According to the present invention an ophthalmic composition may preferably be used for treating inflammatory ocular conditions.

According to the invention an ophthalmic composition is advantageously applied topically to the eye, especially in the form of a solution, a suspension, an ointment, a gel or a solid insert. Such compositions comprise the active ingredient, for example, in a range of from approximately 0.000001 to approximately 5.0% by weight, preferably from approximately 0.001 to approximately 1.0% by weight, or more preferably in the range of from approximately 0.01 to approximately 0.5% by weight and most preferably in the range of from 0.025 to 0.1% by weight. The dose of the active ingredient may depend on various factors, such as mode of administration, requirement, age and/or individual condition. Analogously an above ophthalmic composition may be also topically applied to an ear.

There are used for a corresponding ophthalmic composition customary pharmaceutically acceptable excipients and additives known to the person skilled in the art, for example those of the type mentioned below, especially carriers, stabilizers, solubilizers, tonicity enhancing agents, buffer substances, preservatives, thickeners, complexing agents and other excipients. Examples of such additives and excipients can be found in U.S. Pat. Nos. 5,134,124 and 4,906,613. Such compositions are prepared in a manner known per se, for example by mixing the active ingredient with the corresponding excipients and/or additives to form corresponding ophthalmic compositions. The active ingredient is preferably administered in the form of eye drops, the active ingredient being conventionally dissolved, for example, in a carrier. The solution is, where appropriate, adjusted and/or buffered to the desired pH and, where appropriate, a stabilizer, a solubilizer or a tonicity enhancing agent is added. Where appropriate, preservatives and/or other excipients are added to an ophthalmic composition.

Carriers used in accordance to the present invention are typically suitable for topical or general administration, and are for example water, mixtures of water and water-miscible solvents, such as $C_1$- to $C_7$-alkanols, vegetable oils or mineral oils comprising from 0.5 to 5% by weight hydroxyethylcellulose, ethyl oleate, carboxymethylcellulose, polyvinyl-pyrrolidone and other non-toxic water-soluble polymers for ophthalmic uses, such as, for example, cellulose derivatives, such as methylcellulose, alkali metal salts of carboxymethylcellulose, hydroxymethylcellulose, hydroxyethylcellulose, methylhydroxypropylcellulose and hydroxypropylcellulose, acrylates or methacrylates, such as salts of polyacrylic acid or ethyl acrylate, polyacrylamides, natural products, such as gelatin, alginates, pectins, tragacanth, karaya gum, xanthan gum, carrageenin, agar and acacia, starch derivatives, such as starch acetate and hydroxypropyl starch, and also other synthetic products, such as polyvinyl alcohol, polyvinylpyrrolidone, polyvinyl methyl ether, polyethylene oxide, preferably cross-linked polyacrylic acid, such as neutral Carbopol, or mixtures of those polymers. Preferred carriers are water, cellulose derivatives, such as methylcellulose, alkali metal salts of carboxymethylcellulose, hydroxymethylcellulose, hydroxyethylcellulose, methylhydroxypropylcellulose and hydroxypropylcellulose, neutral Carbopol, or mixtures thereof. The concentration of the carrier is, for example, from 1 to 100 000 times the concentration of the active ingredient.

The solubilizers used for an ophthalmic composition of the present invention are, for example, tyloxapol, fatty acid glycerol poly-lower alkylene glycol esters, fatty acid poly-lower alkylene glycol esters, polyethylene glycols, glycerol ethers or mixtures of those compounds. A specific example of an especially preferred solubilizer is a reaction product of castor oil and ethylene oxide, for example the commercial products Cremophor EL® or Cremophor RH 40®. Reaction products of castor oil and ethylene oxide have proved to be particularly good solubilizers that are tolerated extremely well by the eye. Another preferred solubilizer is tyloxapol. The concentration used depends especially on the concentration of the active ingredient. The amount added is typically sufficient to solubilize the active ingredient. For example, the concentration of the solubilizer is from 0.1 to 5000 times the concentration of the active ingredient.

According to the present invention lower alkylene means linear or branched alkylene with up to and including 7 C-atoms. Examples are methylene, ethylene, 1,3-propylene, 1,2-propylene, 1,5-pentylene, 2,5-hexylene or 1,7-heptylene.

Lower alkylene is preferably linear or branched alkylene with up to and including 4 C-atoms.

Examples of buffer substances are acetate, ascorbate, borate, hydrogen carbonate/carbonate, citrate, gluconate, lactate, phosphate, propionate and TRIS (tromethamine) buffers. Tromethamine and borate buffer are preferred buffers. The amount of buffer substance added is, for example, that necessary to ensure and maintain a physiologically tolerable pH range. The pH range is typically in the range of from 5 to 9, preferably from 6 to 8.2 and more preferably from 6.8 to 8.1.

Tonicity enhancing agents are, for example, ionic compounds, such as alkali metal or alkaline earth metal halides, such as, for example, $CaCl_2$, KBr, KCl, LiCl, NaI, NaBr or NaCl, or boric acid. Non-ionic tonicity enhancing agents are, for example, urea, glycerol, sorbitol, mannitol, propylene glycol, or dextrose. For example, sufficient tonicity enhancing agent is added to impart to the ready-for-use ophthalmic composition an osmolality of approximately from 50 to 1000 mOsmol, preferred from 100 to 400 mOsmol, more preferred from 200 to 400 mOsmol and even more preferred from 280 to 350 mOsmol.

Examples of preservatives are quaternary ammonium salts, such as cetrimide, benzalkonium chloride or benzoxonium chloride, alkyl-mercury salts of thiosalicylic acid, such as, for example, thiomersal, phenylmercuric nitrate, phenylmercuric acetate or phenylmercuric borate, parabens, such as, for example, methylparaben or propylparaben, alcohols, such as, for example, chlorobutanol, benzyl alcohol or phenyl ethanol, guanidine derivatives, such as, for example, chlorohexidine or polyhexamethylene biguanide, or sorbic acid. Preferred preservatives are cetrimide, benzalkonium chloride, benzoxonium chloride and parabens. Where appropriate, a sufficient amount of preservative is added to the ophthalmic composition to ensure protection against secondary contaminations during use caused by bacteria and fungi.

The ophthalmic compositions may comprise further non-toxic excipients, such as, for example, emulsifiers, wetting agents or fillers, such as, for example, the polyethylene glycols designated 200, 300, 400 and 600, or Carbowax designated 1000, 1500, 4000, 6000 and 10 000. Other excipients that may be used if desired are listed below but they are not intended to limit in any way the scope of the possible excipients. They are especially complexing agents, such as disodium-EDTA or EDTA, antioxidants, such as ascorbic acid, acetylcysteine, cysteine, sodium hydrogen sulfite, butyl-hydroxyanisole, butyl-hydroxy-toluene or α-tocopherol acetate; stabilizers, such as a cyclodextrin, thiourea, thiosorbitol, sodium dioctyl sulfosuccinate or monothioglycerol; or other excipients, such as, for example, lauric acid sorbitol ester, triethanol amine oleate or palmitic acid ester. Preferred exipients are complexing agents, such as disodium-EDTA and stabilizers, such as a cyclodextrin. The amount and type of excipient added is in accordance with the particular requirements and is generally in the range of from approximately 0.0001 to approximately 90% by weight.

A cyclodextrin as is referred to within the present invention is either an α-, β- or γ-cyclodextrin itself, a derivative thereof, e.g. a partially etherified derivative as e.g. a hydroxyalkyl ether or a mixture thereof. Examples of cyclodextrin derivatives are alkylated, hydroxyalkylated, carboxyalkylated or alkyloxycarbonyl-alkylated α-, β- or γ-cyclodextrins. Other typical examples are carbohydrate derivatives of cyclodextrins such as mono- or diglycosyl-α-, β- or γ-cyclodextrin, mono- or dimaltosyl-α-, β- or γ-cyclodextrin or panosyl-cyclodextrin. Another parameter which describes the substitution pattern of a cyclodextrin derivative is the degree of substitution (d.s.). A cyclodextrin is composed of several glucose units which have three free hydroxy groups per glucose. Accordingly the d.s. may vary from 0.125 up to 3. In the latter case all free (γ-cyclodextrin has 24) hydroxy groups may be substituted, while in the former case only 1 may be substituted. Preferably the d.s. may vary from 0.125 to 1.5 and more preferably from 0.125 to 0.5.

Preferred cyclodextrins are β- and γ-cyclodextrin, derivatives and mixtures thereof.

Strongly preferred cyclodextrins are hydroxypropyl-β-cyclodextrin, hydroxypropyl-γ-cyclodextrin, dimethyl-β-cyclodextrin and dimethyl-γ-cyclodextrin.

The amount of a cyclodextrin used in accordance with the present invention may preferably range from 0.01–20% by weight, more preferably from 0.1–15% by weight and even more preferably from 1–10% by weight.

The present invention relates also to an ophthalmic composition, which comprises a therapeutically effective amount of diclofenac potassium, a carrier, a solubilizer and another therapeutically effective pharmaceutical agent which may be, for example, an antibiotic, an antiallergic, an anesthetic, another antiphlogistic, a corticosteroide, an agent suitable for lowering intra-ocular pressure, or another drug.

Several animal models are used for the demonstration of the claimed therapeutic efficacy of the ophthalmic compositions comprising diclofenac potassium. In each animal model several ophthalmic reference drugs are administered for comparison.

In a first animal model, the ocular distribution and lens penetration of diclofenac potassium and diclofenac sodium is determined after multiple topical ocular administration of a corresponding eye drop composition. Hence 14C labelled eye drop material is topically administered to the eyes of chinchilla pigmented rabbits (5 instillations, 50 μl each, within 20 minutes). At regular intervals post-instillation (0.5, 1.5, 2.0 hours), the animals are sacrificed and both eyes are removed. Said eyes are microdissected and the ocular distribution of the radioactivity is measured by a standard scintillation beta counting method. The highest concentrations are found in the cornea, and in descending order in the aqueous humor, in the iris ciliary body and in the vitreous. According to this experimental setup, the diclofenac potassium treated animals clearly displayed higher levels of radioactivity in the aforementioned areas than the diclofenac sodium treated animals.

Another animal model is used for the comparison of the ocular anti-inflammatory efficacy of diclofenac potassium in comparison to diclofenac sodium, which model is the arachidonic acid induced uveitis in pigmented rabbits. Repeated instillations of arachidonic acid into the eye of rabbits induce an ocular inflammation, which inflammation significantly increases the flare level in the anterior chamber of rabbits. A laser cell flare meter (LCFM) is used for the quantification of said flare levels. This method is described by e.g. M. Kuchle et al., Ophthalmologe 91, 219(1994), and is a non-invasive method. It has been demonstrated, that the flare determination by LCFM reflects the amounts of proteins comprised in the aqueous humor. These proteins are commonly used as markers in assessing the degree of an inflammation. For the non-invasive evaluation of the efficacy of an anti-inflammatory drug, said drugs are administered by using two instillations one hour and 45 minutes before the induction of an arachidonic acid induced inflammation as described above. A control group of animals is treated with a single instillation of non-preserved saline (Unilarm®). The inflammation process is monitored during 6 hours post-inflammation by the above described LCFM measurements.

In a further animal model the ocular anti-inflammatory efficacy of diclofenac potassium is determined with a traumatic uveitis model. Uveitis is induced in said model by an argon laser iris photocoagulation in pigmented rabbits. Said iris photocoagulation is induced by 500 μm argon laser burns (power 750 mW, duration 0.1 sec). The inflammatory processes resulting therefrom are measured every 30 minutes after the laser induced photo-coagulation, by using the laser cell flare meter (LCFM) technique. For the evaluation of the efficacy of an anti-inflammatory drug, said drugs are again administered by two instillations, one hour and 45 minutes prior to the induction of an inflammation as described above. A control group of animals is treated with instillations of non-preserved saline (Unilarm®). Again the inflammation process is monitored during 6 hours.

In addition to the non invasive LCFM evaluation of the above mentioned animal model, an invasive evaluation is carried out. Therefore the rabbits are sacrificed one hour and in regular intervals after which said eyes have been subjected to the traumatic uveitis by photocoagulation, and the aqueous humor of said rabbit eyes is sampled. The aqueous protein levels, cell counts and prostaglandins (PGE2, PGD2, 6-keto PGF1α) which represent the degree of an inflammation are biochemically investigated and quantified.

Another animal model is used for the induction of a traumatic uveitis. It is the induction of a uveitis by the paracentesis of the anterior chamber of the rabbit eye. In analogy to the previously described laser induced uveitis model, drugs to be tested, are again administered prior to the paracentesis challenge. In this animal model, the animals are again sacrificed at regular intervals, and the inflammatory process is investigated by sampling the aqueous humor of the challenged rabbit eyes. The aqueous protein levels are again analyzed, quantified and then correlated with the degree of an inflammation.

In all the aforementioned animal models, there is clear evidence that animals which are treated with diclofenac potassium benefit from a better efficacy compared to the animals treated with diclofenac sodium.

Typical experimental procedures which illustrate the present invention, but are not intended to limit it in any way, are described below.

EXAMPLE 1

Formulation of diclofenac potassium eye drops (0.1%)

| | |
|---|---|
| diclofenac potassium | 1.00 mg/ml |
| thiomersal | 0.04 mg/ml |
| boric acid | 19.0 mg/ml |
| cremophor EL ® (polyoxyl 35 castor oil) | 50.0 mg/ml |
| tromethamine | 6.0 mg/ml |
| deion. water ad. | 1.0 ml |

EXAMPLE 2

Formulation of diclofenac potassium eye drops (0.05%)

| | |
|---|---|
| diclofenac potassium | 0.50 mg/ml |
| benzalkonium chloride | 0.05 mg/ml |
| disodium edetate | 1.0 mg/ml |
| tyloxapol | 1.0 mg/ml |
| γ-cyclodextrin | 20.0 mg/ml |
| tromethamine | 1.0 mg/ml |
| hydrochloric acid 10% | 1.3 mg/ml |
| sorbitol | 46.0 mg/ml |
| deion. water ad. | 1.00 ml |

EXAMPLE 3

Formulation of non-preserved uni-dose diclofenac potassium eye drops (0.1%)

| | |
|---|---|
| diclofenac potassium | 1.00 mg/ml |
| disodium edetate | 1.0 mg/ml |
| tyloxapol | 0.1 mg/ml |
| dimethyl-β-cyclodextrin | 40.0 mg/ml |
| tromethamine | 1.0 mg/ml |
| hydrochloric acid 10% | 1.3 mg/ml |
| sorbitol | 41.0 mg/ml |
| deion. water ad. | 1.00 ml |

EXAMPLE 4

Formulation of oily eye drops

| | |
|---|---|
| diclofenac potassium | 0.50 mg/ml |
| benzalkonium chloride | 0.1 mg/ml |
| cremophor RH 40 ®, (polyoxyl 40 hydrogenated castor oil) | 20.0 mg/ml |
| castor oil ad. | 1.00 ml |

EXAMPLE 5

Formulation of an eye gel

| | |
|---|---|
| diclofenac potassium | 0.50 mg/g |
| thiomersal | 0.04 mg/g |
| boric acid | 1.8 mg/g |
| cremophor EL ® (polyoxyl 35 castor oil) | 4.0 mg/g |
| tromethamine | 13.0 mg/g |
| carbomer 980 | 4.0 mg/g |
| deion. water ad. | 1.00 g |

EXAMPLE 6

Formulation of an eye gel

| | |
|---|---|
| diclofenac potassium | 1.00 mg/g |
| benzalkonium chloride | 0.1 mg/g |
| tyloxapol | 1.0 mg/g |

-continued

| | |
|---|---|
| mannitol | 30.0 mg/g |
| hydrochloric acid 10% | 1.0 mg/g |
| disodium edetate | 0.5 mg/g |
| chitosan | 10.0 mg/g |
| deion. water ad. | 1.00 g |

EXAMPLE 7

Formulation of an eye ointment

| | |
|---|---|
| diclofenac potassium | 1.00 mg/g |
| phenylethyl alcohol | 5.0 mg/g |
| tyloxapol | 1.0 mg/g |
| disodium edetate | 0.5 mg/g |
| γ-cyclodextrin | 20.0 mg/g |
| deion. water | 140 mg/g |
| cetylstearyl alcohol | 22.0 mg/g |
| liquid paraffin | 207 mg/g |
| white petrolatum | 462 mg/g |
| wool fat | 141.5 mg/g |

EXAMPLE 8

Formulation of diclofenac potassium eye drops (0.05%)

| | |
|---|---|
| diclofenac potassium | 0.5 mg/ml |
| cremophor RH ® (polyoxyl 40 hydrogenated castor oil) | 0.6 mg/ml |
| tromethamine | 1.0 mg/ml |
| disodium edetate | 0.5 mg/ml |
| sorbitol | 49.0 mg/ml |
| benzalkonium chloride | 0.15 mg/ml |
| hydrochloric acid 1N | 5.1 mg/ml |
| water for injections ad | 1.0 ml |
| pH | 7.53 |
| osmolality (mOsmol): | 317 |

EXAMPLE 9

Formulation of diclofenac sodium eye drops (0.1%)

| | |
|---|---|
| diclofenac sodium | 1.0 mg/ml |
| cremophor RH ® (polyoxyl 40 hydrogenated castor oil) | 0.6 mg/ml |
| tromethamine | 1.0 mg/ml |
| disodium edetate | 0.5 mg/ml |
| sorbitol | 49.0 mg/ml |
| benzalkonium chloride | 0.15 mg/ml |
| hydrochloric acid 1N | 5.52 mg/ml |
| water for injections ad | 1.0 ml |
| pH | 7.49 |
| osmolality (mOsmol): | 308 |

EXAMPLE 10

Formulation of an eye drop vehicle

| | |
|---|---|
| cremophor RH ® (polyoxyl 40 hydrogenated castor oil) | 0.6 mg/ml |
| tromethamine | 1.0 mg/ml |
| disodium edetate | 0.5 mg/ml |
| sorbitol | 49.0 mg/ml |
| benzalkonium chloride | 0.15 mg/ml |
| hydrochloric acid 1N | 5.0 mg/ml |
| water for injections ad | 1.0 ml |
| pH: | 7.53 |
| osmolality (mOsmol): | 301 |

EXAMPLE 11

Formulation of diclofenac potassium eye drops (0.1%)

| | |
|---|---|
| diclofenac potassium | 1.0 mg/ml |
| cremophor RH ® (polyoxyl 40 hydrogenated castor oil) | 0.6 mg/ml |
| tromethamine | 1.0 mg/ml |
| disodium edetate | 0.5 mg/ml |
| sorbitol | 49.0 mg/ml |
| benzalkonium chloride | 0.15 mg/ml |
| hydrochloric acid 1N | 5.7 mg/ml |
| water for injections ad | 1.0 ml |
| pH: | 7.35 |
| osmolality (mOsmol): | 314 |

EXAMPLE 12

Changes in aqueous flares (expressed as the area under the kinetic curves (AUC)) for the arachidonic acid induced uveitis model, carried out in pigmented rabbits.

The drugs listed infra (including placebo) are applied topically (30 μl each) to the left eye of pigmented rabbits (chinchilla pigmented female rabbits) one hour before arachidonic acid instillations. Each opposite eye is instilled for control with 30 μl of the vehicle formulation of example 10. Before the instillation of arachidonic acid, the animals are anesthetized with intramuscular injections of 35 mg/kg ketamine (Imalgene 1000®, Rhone Mérieux) and 15 mg/kg xylazine (Rompun-Bayer). Arachidonic acid (0.5% aqueous solution, freshly prepared before use) is then instilled into both eyes of the rabbits with a Hamilton syringe (twice 50 μl). A time interval of 5 minutes is kept between each instillation. The flares are then measured hourly, using an LCFM over a total period of 6 hrs after the arachidonic acid challenge. Before each measurement, the animals are freshly anesthetized with intramuscular injections of 35 mg/kg ketamine (Imalgene 1000®, Rhone Mérieux) and 15 mg/kg xylazine (Rompun-Bayer), in order to completely immobilize the eyes. The LCFM method is similar to a slit lamp microscopy examination. The laser beam of a Kowa FC-1000 LCFM is scanning vertically within a distance of 0.6 mm towards the center of the anterior chamber. Each measurement lasts about 0.5 seconds. Such a measurement is repeated five times for each eye and the average of the photon counts is then calculated and plotted versus the observation time, which lasts in total 6 hours calculated from the induction of the inflammation. The results are summarized below, which show the integrated photon counts of the treated and of the control eyes (AUC(treated) and AUC (control)), representing the overall degree of said induced inflammation over said 6 hours. Accordingly a high AUC number represents a strong inflammation, whereas a low AUC number represents a low degree of inflammation.

The ratio, AUC(treated) divided by AUC(control), is calculated as well. A low ratio value represents a strong anti-inflammatory efficacy, whereas a ratio value of about 1 reflects the substantial absence of an anti-inflammatory effect.

| Drug | AUC(t)reated Mean ± SEM | AUC(c)ontrol Mean ± SEM | Ratio AUC(t)/AUC(c) Mean ± SEM |
|---|---|---|---|
| placebo group (Unilarm ®) | 1616 ± 130 | 1793 ± 171 | 0.93 ± 0.09 |
| diclofenac potassium Example 8 | 99 ± 20 | 1043 ± 186 | 0.1 ± 0.02 |
| diclofenac sodium Example 9 | 558 ± 141 | 1462 ± 270 | 0.46 ± 0.12 |

The AUC(treated) values show the superior efficacy of diclofenac potassium (example 8) in comparison to the efficacy of diclofenac sodium (example 9). The inflammation in the animal group receiving diclofenac potassium is almost totally suppressed. Taking into account the fact that the drug concentration of diclofenac sodium (example 9) is twice the concentration of diclofenac potassium (0.1% versus 0.05%), diclofenac potassium is considered to have more than five fold efficacy of diclofenac sodium.

EXAMPLE 13

Lens penetration and ocular distribution of diclofenac potassium and diclofenac sodium were determined after multiple topical ocular administration of corresponding 14-C labelled eye drop composition into the conjunctival sac of the right eye of pigmented rabbits.

At 0.5, 1.5, 2 hours post-instillation, 5 animals for each time-point and each treatment group were sacrificed and the radioactivity content (in ng-Eq/g of structure) in the cornea, aqueous humor, iris-ciliary body, vitreous, whole blood and plasma was measured. At 2 hours post-instillation, the left eyes were removed and the ocular distribution was measured by a standard scintillation beta counting method. The right lenses were used for autoradiography.

The areas under the curve (AUC: ng-Eq/g of structure versus time) were calculated and statistically compared.

The results indicated that the ocular penetration of diclofenac potassium is much superior in comparison to diclofenac sodium:

Example 8 14-C-diclofenac potassium

| Sampling time (hour) | AUC: (ng-Eq/g) Mean = 5 | SEM |
|---|---|---|
| 0.5 | 58 978 | 19 724 |
| 1.5 | 34 385 | 3 669 |
| 2.0 | 23 114 | 4 093 |

Example 9 14-C-diclofenac sodium

| Sampling time (hour) | AUC: (ng-Eq/g) Mean = 5 | SEM |
|---|---|---|
| 0.5 | 30 342 | 5 721 |
| 1.5 | 20 201 | 5 061 |
| 2.0 | 13 840 | 3 497 |

EXAMPLE 8

14-C-diclofenac potassium

| AUC: (ng-Eq/g) * hour Mean = 5 | SEM |
|---|---|
| 61 056 | 9 131 |

EXAMPLE 9

14-C-diclofenac sodium

| AUC: (ng-Eq/g) * hour Mean = 5 | SEM |
|---|---|
| 33 782 | 3 826 |

The highest concentration were found for both studied drugs in the cornea and in descending order in aqueous humor, iris-ciliary body and vitreous.

EXAMPLE 14 eye drop formulations

| | | |
|---|---|---|
| diclofenac potassium | 1.00 mg | 0.5 mg |
| tromethamine | 1.00 mg | 1.00 mg |
| propylene glycol | 20.5 mg | 20.5 mg |
| hydroxypropyl-γ-cyclodextrin | 20.0 mg | 20.0 mg |
| disodium edetate | 1.00 mg | 1.00 mg |
| benzalkonium chloride | 0.06 mg | 0.06 mg |
| hydrochloric acid 1N | qs | qs |
| water for injections ad | 1.00 ml | 1.00 ml |
| pH | 7.90 | 7.90 |
| osmolality (mOsmol) | 296 | 296 |
| preservative efficacy (Ph. Eur.) | A | A |

The European Pharmacopoeia (Ph. Eur.) describes an efficacy test for antimicrobial preservation. Accordingly a preserved solution is inoculated with micro-organisms, characterized in that $10^5$ to $10^6$ micro-organisms are contained in one milliliter of the challenged preparation. The inoculum used does not exceed 1% of the total volume of said preparation. Five micro-organisms are used for the challenge, each separately namely, pseudomonas aeruginosa, staphylococcus aureus, candida albicans and aspergillus niger. The challenged solutions are kept at room temperature and protected from light. At regular time intervals samples are removed and the number of viable micro-organisms is determined either by plate count or by membrane filtration. For ophthalmic preparations the European Pharmacopoeia recommends criteria "A", which require e.g. that the bacterial micro-organisms are reduced by a factor of 1000, 24 hours after the challenge. Criteria "B" are still acceptable according to the recommendations of the European Pharmacopoeia, and require e.g. that the bacterial micro-organisms are reduced by a factor of 10, 24 hours after the challenge (for details refer to the European Pharmacopoeia, 1994). Accordingly, whenever the preservative efficacy recommendations of the European Pharmacopoeia are referred to herein, this relates to the 1994 version.

EXAMPLE 15 diclofenac potassium eye drop formulations

| | | |
|---|---|---|
| diclofenac potassium | 1.00 mg | 0.5 mg |
| tyloxapol USP | 1.00 mg | 1.00 mg |
| tromethamine | 1.00 mg | 1.00 mg |
| propylene glycol | 19.0 mg | 19.0 mg |
| hydroxypropyl-γ-cyclodextrin | 20.0 mg | 20.0 mg |
| disodium edetate | 1.00 mg | 1.00 mg |
| benzalkonium chloride | 0.05 mg | 0.05 mg |
| hydrochloric acid 1N | qs | qs |
| water for injections ad | 1.00 ml | 1.00 ml |
| pH | 7.96 | 7.98 |
| osmolality (mOsmol) | 305 | 303 |

EXAMPLE 16 eye gel formulation comprising diclofenac potassium

| | | |
|---|---|---|
| diclofenac potassium | 1.00 mg | 1.00 mg |
| tyloxapol USP | 1.00 mg | 1.00 mg |
| tromethamine | 6.50 mg | 6.50 mg |
| propylene glycol | 19.0 | mg |
| sorbitol | 40.0 mg | |
| hydroxypropyl-γ-cyclodextrin | 20.0 mg | 20.0 mg |
| disodium edetate | 1.00 mg | 1.00 mg |
| benzalkonium chloride | 0.05 mg | 0.05 mg |
| carbopol 980 | 3.50 mg | 3.50 mg |
| water for injections ad | 1.00 ml | 1.00 ml |
| pH | 8.06 | 8.00 |
| osmolality (mOsmol) | 298 | 308 |
| viscosity (mPa s) | 450 | 380 |

EXAMPLE 17 eye drops SDU (single dose units, non-preserved)

| | | |
|---|---|---|
| diclofenac potassium | 1.00 mg | 0.5 mg |
| tyloxapol USP | 1.00 mg | 1.00 mg |
| tromethamine | 1.00 mg | 1.00 mg |
| propylene glycol | 19.0 mg | 19.0 mg |
| hydroxypropyl-γ-cyclodextrin | 20.0 mg | 20.0 mg |
| disodium edetate | 1.00 mg | 1.00 mg |
| hydrochloric acid 1N | qs | qs |
| water for injections ad | 1.00 ml | 1.00 ml |
| pH | 7.95 | 7.98 |
| osmolality (mOsmol) | 301 | 300 |

EXAMPLE 18 preservative efficacy

| | | | |
|---|---|---|---|
| diclofenac sodium | 1.00 mg | 1.00 mg | — |
| diclofenac potassium | — | — | 1.00 mg |
| 2-hydroxypropyl-β-cyclodextrin | 15.0 mg | 20.0 mg | 15.0 mg |
| 2-hydroxyethyl-β-cyclodextrin | 15.0 mg | 20.0 mg | 15.0 mg |
| hydroxypropyl-γ-cyclodextrin | — | — | — |
| boric acid | 13.0 mg | 13.0 mg | 13.0 mg |
| borax | 8.6 mg | 8.6 mg | 8.6 mg |
| methylparabene | 0.26 mg | 0.26 mg | 0.26 mg |
| propylparabene | 0.14 mg | 0.14 mg | 0.14 mg |
| sodium hydroxide 0.1 N | 8.0 mg | 6.0 mg | — |
| water for injections ad | 1.0 ml | 1.0 ml | 1.0 ml |
| pH: | 7.80 | 7.86 | 7.89 |
| Osmolality (mOsmol) | 332 | 325 | 308 |
| preservative efficacy Ph. Eur. | r.n.m. | r.n.m. | r.n.m. |

r.n.m.(recommendations not met), the preservative efficacy of the corresponding composition does not meet the recommendations of the European Pharmacopoeia.

EXAMPLE 19 preservative efficacy

| | | | |
|---|---|---|---|
| diclofenac sodium | — | — | 1.00 mg |
| diclofenac potassium | 1.00 mg | 1.00 mg | — |
| 2-hydroxypropyl-β-cyclodextrin | 20.0 mg | — | — |
| 2-hydroxyethyl-β-cyclodextrin | 20.0 mg | — | — |
| hydroxypropyl-γ-cyclodextrin | — | 20.0 mg | 20.0 mg |
| boric acid | 13.0 mg | 13.0 mg | 13.0 mg |
| borax | 8.6 mg | 8.6 mg | 8.6 mg |
| methylparabene | 0.26 mg | 0.26 mg | 0.26 mg |
| propylparabene | 0.14 mg | 0.14 mg | 0.14 mg |
| sodium hydroxide 0.1 N | 2.0 mg | 0.3 mg | 0.4 mg |
| water for injections ad | 1.0 ml | 1.0 ml | 1.0 ml |
| pH: (8 ± 0.3) | 7.90 | 7.89 | 7.92 |
| Osmolality (mOsmol), (300 ± 30) | 323 | 288 | 285 |
| preservative efficacy Ph. Eur. | r.n.m. | r.n.m. | r.n.m. |

What is claimed is:

1. A method for treating glaucoma which is associated with administered or endogenous glucocortioids, said method comprising the step of administering a therapeutically effective amount of an ophthalmic composition comprising diclofenac potassium and a carrier.

2. The method of claim 1 wherein said ophthalmic composition further comprises a stabilizer.

3. The method of claim 2 wherein said stabilizer is selected from the group consisting of vitamin E, vitamin E derivatives and mixtures thereof.

4. The method of claim 1 wherein said ophthalmic composition further comprises a solubilizer.

5. The method of claim 2 wherein said stabilizer is a cyclodextrin.

6. The method of claim 1 wherein said ophthalmic composition comprises from 0.000001 to 5% by weight of diclofenac potassium.

7. The method of claim 1 wherein said ophthalmic composition comprises from 0.001 to 1% by weight of diclofenac potassium.

* * * * *